United States Patent
Chen et al.

(10) Patent No.: US 7,854,609 B2
(45) Date of Patent: *Dec. 21, 2010

(54) DENTAL APPLIANCE WEAR INDICATION

(75) Inventors: Jennifer C. Chen, San Francisco, CA (US); Chunhua Li, Cupertino, CA (US); Anthony Morefield, San Jose, CA (US)

(73) Assignee: Align Technology, Inc., San Jose, CA (US)

(*) Notice: Subject to any disclaimer, the term of this patent is extended or adjusted under 35 U.S.C. 154(b) by 768 days.

This patent is subject to a terminal disclaimer.

(21) Appl. No.: 11/799,979

(22) Filed: May 3, 2007

(65) Prior Publication Data

US 2007/0207440 A1   Sep. 6, 2007

Related U.S. Application Data

(63) Continuation-in-part of application No. 10/949,717, filed on Sep. 24, 2004, now Pat. No. 7,553,157.

(51) Int. Cl.
*A61C 3/00* (2006.01)
(52) U.S. Cl. .......................................... 433/6
(58) Field of Classification Search ............... 433/6, 433/24
See application file for complete search history.

(56) References Cited

U.S. PATENT DOCUMENTS

| | | | | |
|---|---|---|---|---|
| 2,835,628 A | * | 5/1958 | Saffir | 433/39 |
| 3,533,163 A | | 10/1970 | Kirschenbaum | |
| 3,813,781 A | * | 6/1974 | Forgione | 433/68 |
| 3,885,310 A | | 5/1975 | Northcutt | |
| 4,255,138 A | | 3/1981 | Frohn | |
| 4,629,424 A | | 12/1986 | Lauks et al. | |
| 4,741,700 A | * | 5/1988 | Barabe | 433/229 |
| 4,818,542 A | | 4/1989 | DeLuca et al. | |
| 4,968,251 A | * | 11/1990 | Darnell | 433/216 |
| 5,049,077 A | * | 9/1991 | Goldin et al. | 433/229 |
| 5,194,003 A | * | 3/1993 | Garay et al. | 433/215 |
| 5,645,420 A | * | 7/1997 | Bergersen | 433/6 |
| 5,651,671 A | | 7/1997 | Seay et al. | |
| 5,975,893 A | | 11/1999 | Chishti et al. | |
| 5,980,246 A | | 11/1999 | Ramsay et al. | |

(Continued)

FOREIGN PATENT DOCUMENTS

WO   WO 02/058583   8/2002

(Continued)

OTHER PUBLICATIONS

Benson, James R. "Highly Porous Polymers". American Laboratory, Apr. 2003, pp. 1-12.

(Continued)

*Primary Examiner*—Ralph A Lewis
(74) *Attorney, Agent, or Firm*—Brooks, Cameron & Huebsch, PLLC

(57) ABSTRACT

The present disclosure includes method, system, apparatus, and indicator embodiments. For example, one system for monitoring orthodontic treatment includes an appliance for placement over one or more teeth and multiple wear indicators including at least a first wear indicator having a first wear rate and a second wear indicator that has a second wear rate that is different from the first.

27 Claims, 5 Drawing Sheets

U.S. PATENT DOCUMENTS

| | | | |
|---|---|---|---|
| 6,099,303 | A | 8/2000 | Gibbs et al. |
| 6,309,215 | B1 | 10/2001 | Phan et al. |
| 6,607,382 | B1 | 8/2003 | Kuo et al. |
| 7,194,781 | B1 * | 3/2007 | Orjela .................. 15/250.001 |
| 7,553,157 | B2 * | 6/2009 | Abolfathi et al. ............... 433/6 |
| 2003/0008259 | A1 * | 1/2003 | Kuo et al. ...................... 433/6 |
| 2006/0068353 | A1 | 3/2006 | Abolfathi et al. |
| 2006/0166157 | A1 * | 7/2006 | Rahman et al. ................ 433/6 |
| 2008/0118882 | A1 * | 5/2008 | Su ............................... 433/2 |

FOREIGN PATENT DOCUMENTS

| WO | WO 2005/114183 | 12/2005 |
|---|---|---|
| WO | WO 2006/060547 | 6/2006 |

OTHER PUBLICATIONS

Brannon-Peppas, Lisa. "Biomaterials: Polymers in Controlled Drug Delivery". Medical Devicelink, Medical Plastics and Biomaterials Magazine, Nov. 1997, 19 pgs.

Landgraf, William, et al. "Polymer Microcarrier Exhibiting Zero-Order Release". Drug Delivery Technology, vol. 3, No. 1, pp. 1-14.

Lawrence, Herenia P. "Salivary Markers of Systemic Disease:Noninvasive Diagnosis of . . . ". Journal of the Canadian Dental Association, Mar. 2002, vol. 68, No. 3, pp. 170-174.

Middleton, John C., et al. "Synthetic Biodegradable Polymers as Medical Devices". Medical Plastics and Biomaterials Magazine, MPB Article Index, 1998, 14pp.

Nishanian, Parunag, et al. "Oral Fluids as an Alternative to Serum for Measurement . . . ". Clinical and Diagnostic Laboratory Immunology, vol. 5, No. 4, Jul. 1998, pp. 507-512.

Sigma-Aldrich Co."Tutorial . . . ". http://www.sigmaaldrich.com/area_of_interest/ organic_inorganic_chemistry/materials_science/biocompatible_biocompatible_polymers.html, 2004 3 pg.

Svec, Frantisek, et al. "Molded Rigid Monolithic Porous Polymers: An Inexpensive, Efficient, and Versatile Alternative to Beads . . . ".Ind. Eng. Chem. Res. 1999, pp. 34-48.

Van Der Eijk, A.A., et al. "Paired Measurements of quantitative hepatitis B virus DNA in saliva and serum of chronic . . . ". Journal of Clinical Virology 29, 2004, pp. 92-94.

Unknown. Excerpt from a reference on water-soluble polymers, date unknown, 2 pgs.

* cited by examiner

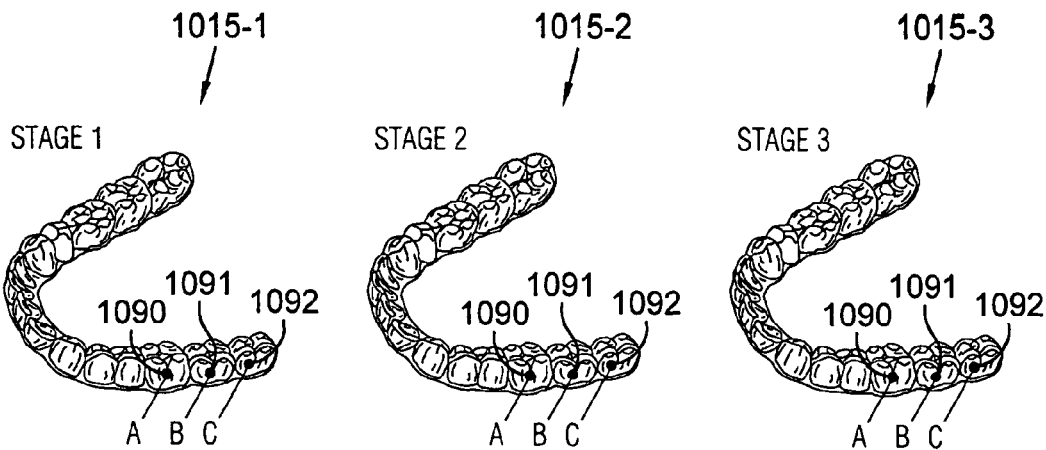

FIG. 10

|  | ○ WHITE |
|  | ⊛ DARK BLUE |
|  | ⊘ LIGHT BLUE |

| 1193 | 1194 | 1195 |
|---|---|---|
| C⊛ ⊛B ⊘A | SELECT AND ATTACH ONE A INDICATOR TO EACH OF THE REMAINING ALIGNER STAGES 4, 5, AND 6 | ⊘ BASELINE COLOR FADED |
| ⊛ ⊛ ○ | SELECT AND ATTACH ONE A INDICATOR TO EACH OF THE REMAINING ALIGNER STAGES 4, 5, AND 6 | ○ BASELINE COLOR CLEAR |
| ⊛ ⊘ ○ | SELECT AND ATTACH ONE B INDICATOR TO EACH OF THE REMAINING ALIGNER STAGES 4, 5, AND 6 | ⊘ BASELINE COLOR FADED |
| ⊛ ○ ○ | SELECT AND ATTACH ONE B INDICATOR TO EACH OF THE REMAINING ALIGNER STAGES 4, 5, AND 6 | ○ BASELINE COLOR CLEAR |
| ⊘ ○ ○ | SELECT AND ATTACH ONE C INDICATOR TO EACH OF THE REMAINING ALIGNER STAGES 4, 5, AND 6 | ⊘ BASELINE COLOR FADED |
| ○ ○ ○ | SELECT AND ATTACH ONE C INDICATOR TO EACH OF THE REMAINING ALIGNER STAGES 4, 5, AND 6 | ○ BASELINE COLOR CLEAR |

FIG. 11

DENTAL APPLIANCE WEAR INDICATION

RELATED APPLICATIONS

The present application is a continuation in part (CIP) of U.S. patent application Ser. No. 10/949,717, filed on Sep. 24, 2004 now U.S. Pat. No. 7,553,157, the disclosure of which is incorporated in its entirety herein by reference.

BACKGROUND

The present disclosure is related to systems and methods for dental appliance compliance indication.

As noted in commonly owned U.S. Pat. No. 6,607,382 entitled "Methods and systems for concurrent tooth repositioning and substance delivery," the content of which is incorporated herewith, the repositioning of teeth may be accomplished with the use of a series of removable elastic positioning appliances such as the Invisalign® system available from Align Technology, Inc., the assignee of the present disclosure. Such appliances have a thin shell of elastic material that generally conforms to a patient's teeth but is slightly out of alignment with an initial or immediately prior tooth configuration. Placement of the elastic positioner over the teeth applies controlled forces in specific locations to gradually move the teeth into the new configuration. Repetition of this process with successive appliances including new configurations eventually moves the teeth through a series of intermediate configurations or alignment patterns to a final desired configuration. A full description of an exemplary elastic polymeric positioning appliance is described in U.S. Pat. No. 5,975,893, and in published PCT application WO 98/58596, the content of these documents are incorporated by reference for all purposes.

The appliance is effective in repositioning teeth when it is placed over the patient's teeth. In some implementations, it is desirable to wear these appliances most of the day (e.g., all of the time except when eating and maintaining oral hygiene, such as by brushing or flossing). Although easy and convenient to wear, the patient may not wear the appliance as prescribed by the treatment professional. Extended removal of the appliance, for any reason beyond what is recommended, interrupts the treatment plan and lengthens the overall period of treatment. Since the appliance is removable by the patient, the treatment professional has to rely on the patient to comply with the prescription.

Additionally, there may be many variables and differences in each patient's oral environment and, therefore, one type of compliance indicator may not likely be enough to last for a desired period of wear in every person. Some examples of the factors that may change the wear rate include an amount of saliva produced, one or more tooth anatomies or locations, a composition of saliva, an analysis of sleep habits of a patient, an amount of liquid consumption, and one or more types of liquid consumed, among other criteria. These factors can make the analysis of compliance based upon a wear indicator difficult due to the different wear rates that different people may have.

BRIEF DESCRIPTION OF THE DRAWINGS

FIG. 10 shows a number of appliances for use in various stages of a dental treatment process.

FIG. 11 shows a table indicating the meaning of various combinations of wear on appliance indicators.

SUMMARY

An apparatus for monitoring orthodontic treatment compliance includes an appliance adapted to be worn over one or more teeth; and a compliance indicator mounted on the appliance or teeth to indicate compliance.

Advantages of the system include one or more of the following. The apparatus provides better data for communicating device compliance with patients, including: increased patient knowledge and recall of appliance usage; increased compliance in wearing the dental appliance, and increased patient satisfaction as a result. The apparatus provides a channel of self-monitoring for the patient. The apparatus also reduces patient's anxiety levels without requiring verbal or written instructions since device usage is self-evident. The treatment professional also has better information on patient progress during the treatment.

DESCRIPTION

Figure 1:
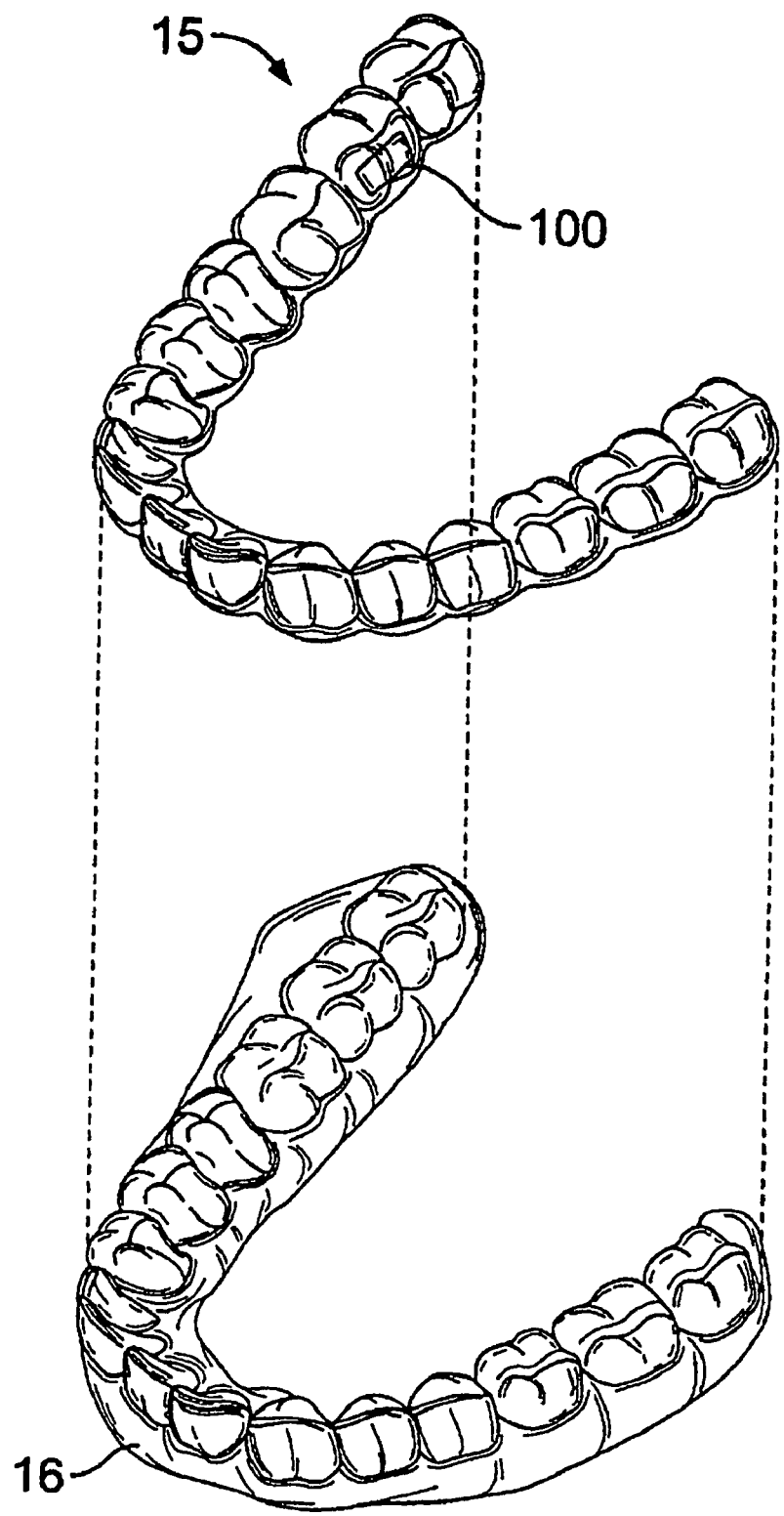
FIG. 1 shows an exemplary compliance indicator.

FIG. 1 shows an exemplary removable appliance 15 adapted to fit over teeth on a jaw 16. A usage indicator 100 can be mounted on one tooth or on the appliance 15 to indicate patient compliance.

In one implementation, the indicator 100 can be a coat on a tooth or an appliance with a chemical agent. Alternatively, the indicator 100 can be an electrical agent, optical agent or mechanical agent that indicates appliance wearage. In some embodiments, the indicator agent is inactive until contact with liquid or electrical agent, optical agent or mechanical agent that indicates appliance wearage. In some embodiments, the indicator agent is inactive until contact with liquid or moisture. Alternatively, release of the agent can be stimulated by liquid or moisture. Thus, in one case, upon wearing, oral fluids activates the agent and allows the agent to seep out and indicate compliance. Alternatively, oral fluids such as saliva, among others, can seep in to activate the agent to indicate compliance.

In another embodiment, the appliance can release a coloring agent to the oral environment when the appliance is worn over the teeth. Such mechanisms may include a layer which includes the agent. The layer may be formed over at least a portion of the surfaces of the repositioning appliance. These surfaces include both the cavity surfaces, the surfaces within the cavities which contact the teeth when in place, and the external surfaces, the surfaces of the appliance which contact the cheeks and lips when in place. The layer may be of various materials and may take a variety of forms. For example, the layer may consist essentially of the agent. In other words, the agent may be attached directly to a surface of the polymer shell of an elastic repositioning appliance. This may be achieved by applying the agent (optionally in an inert carrier or diluent) itself to the surface utilizing a number of methods, such as spraying, painting and/or dipping. When the repositioning appliance is placed over the patient's teeth, the agent may then be released to the oral environment.

Alternatively, the layer may include the agent present in or on a carrier or binder which promotes adhesion or attachment to the appliance and/or which creates a matrix from which the agent can be released by diffusion or dissolution. In some embodiments, the agent is dissolved in the carrier or binder. In this case, the agent may be provided in powder or similar form and dissolved in a liquid solvent. The result may be a solution which may be applied to a surface of the shell, typically by spraying, painting, and/or dipping, to form a coating or film. When the repositioning appliance is placed over the patient's teeth, the compliance indicating agent may then be released from the coating to the oral environment. Release may be due to activation or deactivation of the carrier or any other releasing mechanism, such as by enzymes or proteins in oral fluids. Or release may be due to degradation of the carrier by contact with, for example, oral fluids. In some cases, the binder or carrier may evaporate upon application to the layer to the surface leaving the agent behind. In these cases, the agent may be released in a similar fashion as when the agent is directly attached to the surface, as described above. It may be appreciated that any suitable agent, such as fluoride materials, antibiotics or other drugs or medications, vitamins, bleaching materials, and/or breath fresheners, may be delivered to the oral environment in this manner.

In another embodiment, the agent is encapsulated or suspended in the layer. A common material for suspension of an agent is a semisolid material, such as a gel, jelly, or putty. Such a material may be applied to a surface of the shell by spraying, painting, and/or dipping to form a coating or film. Here, as in all cases, suspension is not limited to a scientific definition and may refer to any situation in which a carrier holds, contains, supports, or otherwise includes an agent. Alternatively or in addition, the semisolid material may be deposited in the cavities of the polymer shell which are shaped to receive the teeth. The cavities may be filled to any desired level. When the repositioning appliance is positioned over the teeth, the teeth will directly contact the semisolid material in the cavities and displace any extra material as the teeth are inserted into the cavities. Therefore, it is desired to fill the cavities to a level which will avoid excess overflow of the material from the appliance. Delivery of an agent by use of a semisolid suspension material is common in bleaching treatments and fluoride treatments, for example. However, such treatments apply the material with the use of a tray or generic appliance which does not apply repositioning forces to the teeth. By modifying a repositioning appliance, as described above, orthodontic treatment may continue throughout the delivery of such agents. It may be appreciated that any agent, particularly fluoride materials, antibiotics, bleaching materials, and breath fresheners, may be delivered to the oral environment in this manner.

Another common material for encapsulation or suspension of an agent is a controlled-release material. Thus, the layer may be of a rate-controlling material wherein the rate controlling material controls the rate at which the agent is released from the layer. Controlled-release or rate-controlled materials deliver a predetermined amount of an agent at a predetermined rate. Often such delivery maintains a steady-state concentration of an agent in an environment within a desired therapeutic range for a prolonged period of time. Thus, a prescribed dosage may be delivered. In addition, the ability to sustain delivery eliminates the need for repeated applications of the agent for dosed delivery to the oral environment.

Although such controlled release materials may be provided as a semisolid material, such as a gel, jelly, or putty, as described above, these materials may also be provided as a solid material which is attached to the polymeric shell of the repositioning appliance. One type of controlled-release material includes a polymer matrix membrane within which finely dispersed particles of an agent are suspended. The agent may diffuse through the matrix membrane according to a concentration gradient. Alternatively or in addition, the agent may be released by degradation of the polymer matrix membrane material. In either case, the controlled-release material may be provided as a sheet which may be laminated to a surface of the shell. The controlled-release sheet may be layered with the elastomeric polymer and vacuum formed over a mold to form the repositioning appliance. The controlled-release material may be arranged so that it is present on the inside or outside surfaces of the appliance depending on the material and desired application. Or, the controlled-release sheet may be laminated or bonded to a surface of the polymeric shell after forming to supply agent delivery in desired areas. Alternatively, the controlled-release material may be provided as a tablet or similar mass which may be inserted into the polymeric shell of the repositioning appliance. The agent may then elute from the tablet into the oral environment over time.

In another embodiment, the agent may be held within pores of a material and may elute out at a controlled rate from the pores. The agent itself may be absorbed into the pores of the material, or the agent may be suspended in a carrier which is absorbed into the pores of the material. In the latter case, the agent may be released from the carrier by diffusion and/or by controlled degradation of the carrier material. This may incorporate a rate-controlling mechanism in addition to the controlled-release of the agent from the pores. As mentioned, in some cases, material to release the agent. It may be appreciated that the agent may be released by a combination of any of the release methods.

In a further embodiment, the polymeric shell of the repositioning appliance itself includes a controlled-release material containing the agent. In this case, at least a portion of a polymeric shell is formed from a controlled release material wherein the rate controlling material controls the rate at which the agent is released from the shell. As previously described, the controlled-release material may be a provided in the form of a sheet. Thus, the sheet of controlled-release material may be vacuum formed over a mold of the patient's teeth to form a repositioning appliance itself. In this manner, no additional elastomeric materials may be needed to form the appliance. The controlled-release material may be a polymer matrix membrane, a porous material, or any suitable material. Controlled-release may be designed so that the elution rate of the agent corresponds to the repositioning rate of the teeth. The agent may elute throughout the repositioning process, concluding as the teeth reach the desired arrangement prescribed by the appliance.

In a still further embodiment, the releasing mechanism coupled to at least some of the repositioning appliances includes a reservoir formed in the shell of the appliance in addition to the cavity which receives the teeth. Typically, a rate controlling membrane is disposed over the reservoir wherein the rate controlling membrane controls the rate at which the substance is released from the reservoir. The reservoir may be pre-filled or pre-loaded with an agent or substance for delivery. In this case, the appliance may be ready for insertion or use upon removal from any packaging without the need of loading the appliance with the agent for delivery. If the releasing mechanism is designed for a single delivery period, the appliance may be worn throughout the prescribed repositioning period and then disposed of. If the releasing mechanism is designed for multiple delivery periods, the reservoir may be replenished with the agent to be released any number of times throughout the prescribed repositioning period. It may be appreciated that any agent, particularly fluoride materials, antibiotics, bleaching materials, and breath fresheners, may be delivered to the oral environment in this manner.

In some instances, it may be desirable to change a visual characteristic of the polymeric shell of an oral appliance. Such appliances include a polymeric shell having a cavity shaped to be removably placeable over the teeth and a material on or within the shell that changes a visual characteristic of the shell. Such a change is typically in response to a change in the environment. In some cases, the visual characteristic is a color, such as green, red, or blue. Thus, the appliance may appear colored or a particular color under certain environmental conditions, either in the oral environment or when removed. The described material may be a dye which changes color in response to a change in temperature. For example, the dye may change color when the appliance is removed from the mouth and changes temperature from body temperature (37 degree C.) to room temperature (25 degree C.). Similarly, the dye may change color when the appliance is rinsed with cool water.

The appliance can be used to provide an intra-oral drug delivery system. In addition to the agents described above, other compounds can be used as well. For example, a drug coated appliance can be used to deliver desensitizing medication to sensitive teeth. The drug substance can simply be a small amount of the active ingredient in a desensitizing toothpaste or gel, such as Sensodyne®. The desensitizing agent is dispersed throughout the surface of the appliance and is delivered, at a substantially constant rate, to the patient's sensitive teeth for a relatively extended period of time.

Although the appliance may be pre-loaded with the agent and ready for use upon removal from any packaging, appliances that are not pre-filled or pre-loaded may require loading prior or immediately prior to placing the appliance over the teeth. Loading may include placing the agent in a teeth-receiving cavity. As described previously, the cavities may be filled to any desired level. When the appliance is positioned over the teeth, the teeth will directly contact the agent in the cavities as the teeth are inserted into the cavities. Alternatively, loading may include placing the agent into an agent release reservoir in the appliance immediately prior to placing the appliance over the teeth. The agent will then elute from the reservoir into the oral environment when the appliance is in place over the teeth. The elution rate may be controlled by a controlled release membrane which separates the reservoir from the surrounding environment. Loading may also include adhering a rate controlling material containing the agent to a surface of the appliance prior to placing the appliance over the teeth. Such a material may include a polymer matrix membrane which may be removably or permanently adhered to the polymeric shell of the appliance in desired areas for delivery of the agent. And finally, loading may include absorbing the agent into a porous material on or within the appliance immediately prior to placing the appliance over the teeth.

Mechanisms for releasing the agent may include a number of embodiments, including any such mechanisms previously described. Typically, mechanisms for releasing the agent includes a layer including the agent, as previously described, and coupling includes adhering the layer to at least a portion of a surface of the appliance. When the layer consists essentially of the agent, adhering may involve coating, spraying, dipping, or painting the agent on the surface of the appliance. Thus, a pre-formed appliance may simply be coated with the agent prior to insertion in the patient's mouth. When the layer includes an agent present in or on a carrier or binder, adhering may involve attaching the carrier or binder a surface of the appliance. Similarly, when the agent is encapsulated in the layer, the layer may be attached to the surface of the appliance. The layer may include a sheet of rate controlling material wherein the rate controlling material controls the rate at which the agent is released from the layer. In this case, the sheet may be bonded to the surface of the appliance with an adhesive. Alternatively, the sheet may be attached to the surface by press fitting. The sheet and the surface may each be shaped so that they snap or fit together by pressing them together. For example, the sheet may have a formed protrusion and the surface a formed inset, wherein the protrusion fits into the inset when pressed upon the inset and holds the sheet in place. In many instances, the appliance may be porous or have a reservoir which can be loaded with a desired agent at any time the treating professional and/or the patient decide that it is appropriate. For example, an appliance can be immersed in a solution of the agent, allowing the appliance to absorb or adsorb the agent at a particular time.

In addition, the sheet may be pre-formed to a shape adapted for fitting against the surface of the appliance or a surface of the teeth or gingiva. For example, the sheet may be pre-formed to reflect the shape of the surface of one or more teeth or the gingiva, particularly along the gingival margin. The preformed sheet may then be held against that surface when the sheet is coupled to the appliance and the appliance is placed over the teeth. Coupling may involve any mechanism of attaching the sheet to the appliance. In particular, the pre-formed sheet may further include an adhesive layer which may provide bonding of the sheet to the surface of the appliance.

The material to make to the appliance of FIG. 1 can be supplemented with additional fillers such as electrically conducting fillers, magnetic fillers, illuminating fillers, piezoelectric fillers, and/or light sensitive fillers. The material properties of the appliance made with or without these additional fillers such as modulus, electrical resistance, material permeability, and birefringence (degree of orientation of the material or stress), illuminating patterns or patterns under special light sources may change after the appliance is worn over time, as these properties are altered due to changes in structure, organization, and/or spatial spacing between the fillers. For example, it is well established that electrical conductivity of filled composites scales with filler volume concentration according to percolation theory. Therefore, mechanical deformation or thermal expansion of the non-conductive polymer matrix will lead to increased average inter-filler spacing, or decreased filler volume concentration, and consequently decreased electrical conductivity. Examples of electrically conductive fillers include metals, graphite, electrically conductive polymers, semiconductors, and superconductors. These changes in properties can be used as an indicator for compliance and can be diagnosed by instrumentation. Similarly, separation of conductive fillers will also lower thermal conductivity, which can also be measured by instrumentations. If the fillers have magnetic behavior in the presence of external stimulation, such as diamagnetics (Cu, Au, Ag, etc.) and paramagnetics (e.g. Al, Cr, Na, Ti, Zr, etc.); or exhibit intrinsic magnetic properties, such as ferromagnetics (Fe, Co, Ni, etc.), antiferromagnetics (e.g. MnO), and ferromagnetics (MFe$_2$O$_4$), then separation of the filler spacing due to mechanical deformation of the polymer matrix can also lead to decreases in magnetic properties above the Curie temperature. Mechanical deformation of composites with illuminating fillers, such as those that exhibit luminescence, fluorescence, or phosphorescence, will result in decreased illumination intensity. Bending deformation or displacement of piezoelectric fibers can result in electrical potentials which can be either measured, or used to activate other electrically driven indicators (e.g. low power LED light). Fillers with optical properties which depend on external electric field, for example those that shift their absorption coefficients in the UV, IR, or visible spectrum can also serve as indicator of matrix deformation.

Figure 2A:
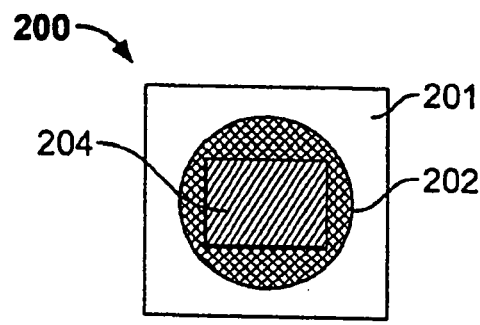
FIGS. 2A-2C show a first embodiment of the compliance indicator of FIG. 1.

Referring now to FIG. 2A, an embodiment of an indication attachment device 200 is shown. The indication attachment device 200 includes a polymer well 201, and the well 201 includes a semi-permeable membrane 202. The membrane 202 allows a two-way flow between the well 201 and an interface to the oral environment. Within the well 201, a material 204 such as a dyed material is provided.

In some embodiments, the dyed material 204 is a releasable material, such as dyed poly(vinylsiloxane) (PVS) material. The PVS material is used to hold the dye, and the membrane 202 can be a cellulose acetate membrane. Those skilled in the art will understand that other releasable materials such as polyether, polyurethane, ethyl vinyl acetate can also be manipulated to result in the teachings of this patent.

In another embodiment, the well material 204 can be an enzyme or a reactor that reacts with enzymes from the oral fluids. When oral fluids or enzyme from the oral fluids enters the well, the material 204 reacts with the enzyme to provide an indication. Alternatively, a pH indicator can be used as the material 204. In yet another embodiment, the membrane 202 can be silicon instead of PVS.

In another embodiment, the polymer can be water-soluble polymer that includes water-soluble polymers, lightly cross-linked hydrogels, and high molecular weight with hydrogen bonding plastics that demonstrate some limited water resistance. Natural-based water-soluble polymers include starch, starch-oxided, cellulose, cellulose-alkoxylated, cellulose-carboxyalkylated, chitin, chitosan, pectins, hyaluronic acid, proteins, and lignin. Water-soluble polymers can also be created from synthetic raw material through polymerization by addition/vinyl, condensation, and ring-opening. Examples of these types of polymers are poly(vinyl alcohol), polyesters, and poly(alkylene oxides). The hydrolytic instability of biodegradable polymers is advantageous because the presence of the oral fluids will facilitate the degradation of the polymer.

Figure 2B:
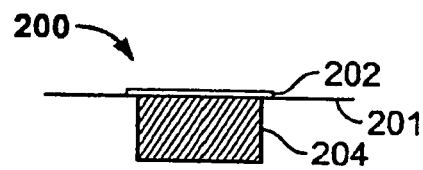
Figure 2C:
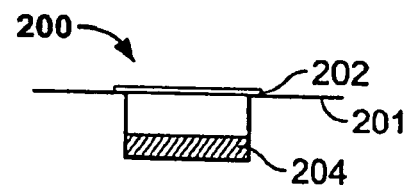

Referring now to FIG. 2B, a cross-sectional view of the compliance indication attachment device (compliance indicator) 200 is shown. As viewed therein, the membrane 202 is positioned above the polymer well, chamber, or housing 201 with the releasable material and or dye 204 enclosed therein. As shown in FIG. 2C, after a predetermined period of time, for example two weeks, a portion of the dyed PVS material 204 has seeped out causing a change in appearance of the indication attachment device. The dye is released while the PVS stays inside the device. In this case, a color change can occur or alternatively, the volume of the material has changed, in this case it has reduced in size.

In some embodiments, the compliance indicator 200 has a clear, tooth-colored, or esthetically pleasing polymer reservoir well, chamber, or housing 201. A transparent or translucent semi-permeable membrane 202 separates the content within the reservoir chamber 201 from the external oral environment. The content(s) within the reservoir chamber 201 depends on the overall strategy to monitor compliance. In one implementation, contents diffuse out from the reservoir chamber 201, through the membrane 202, into the external environment. For example: the content can be an FDA approved visible dye which diffuses from the chamber 201, through the membrane 202, and into the external oral environment. When the content is emptied, the content color diminishes in brightness and value. Colorants that are permitted for direct addition to human food by the US FDA include annatto extract, beta-carotene, beet powder, canthaxanthin, caramel color, carrot oil, cochineal extract (carmine); cottonseed flour, fruit juice, paprika, riboflavin, saffron, turmeric, vegetable juice, FD&C Blue No. 1 (brilliant blue) and No. 2 (indigotine), FD&C Green No. 3 (fast green FCF), FD&C Red No. 3 (erythrosine) and No. 40 (allura red), FD&C Yellow No. 5 (tartrazine) and No. 6 (sunset yellow). Other food colorants such as those found at FDA's Center for Food Safety and Applied Nutrition website: http://www.cfsan-.fda.gov/.about.dms/col-toc.html can be used as well.

In another implementation, matter from the external environment diffuse in, and reacts with the contents 204 within the reservoir chamber 201. For example, glucose molecules from the external environment diffuse through the membrane 202, and reacts with enzymes inside the content and the resultant enzymatic products interact with other reactants inside the content to cause color change. As more glucose molecules diffuse in, content color increases in brightness and value. A convenient enzyme system is glucose oxidase and horseradish peroxidase. The first enzyme, glucose oxidase, catalyzes the oxidation of glucose to form gluconic acid and hydrogen peroxide. Hydrogen peroxide then reacts with 3-3,5,5'-tetramethylbenzidine (TMB) under catalytic action of horseradish peroxidase to convert yellow TMB to green. Other colorants, such as potassium iodide (green to brown) may also be used. These enzymes can be immobilized within the chamber. The rate of reaction, and hence color change, can be controlled by selecting the permeability of the membrane 202, the concentration of reactants inside the chamber 201, and the method of delivery. The rate of reaction or concentration of the glucose molecules can also be detected through spectroscopy or other analytical testing. Test results will correlate with compliance to treatment.

Figure 3A:
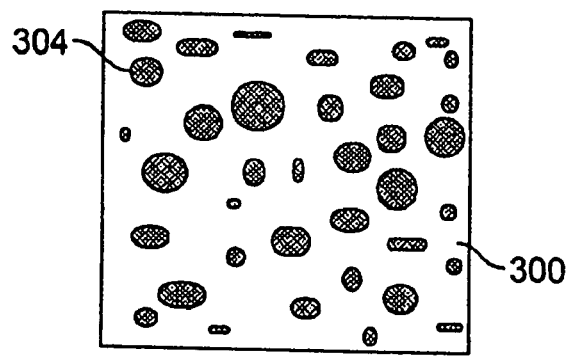
FIGS. 3A-3B show a second embodiment of the compliance indicator of FIG. 1.
Figure 3B:
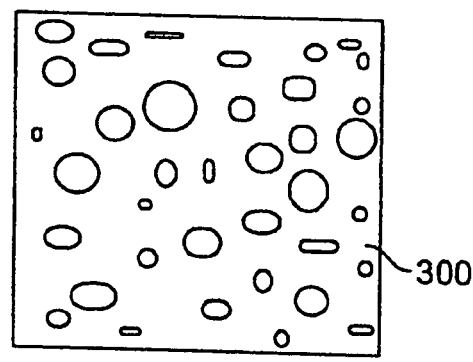

Referring now to FIGS. 3A and 3B, another embodiment of an indication attachment device is shown. In the embodiment of FIG. 3A, a porous polymer material is provided on a sheet 300. The polymer material is disposed on the sheet 300 as one or more containers 304. The container 304 may be a well as disclosed above in the discussion of FIGS. 2A-2C. After a predetermined period of usage, the polymer material changes appearance, for instance, changes either to the color or the size as shown in FIGS. 2B-2C. Other implementations can include colored polymers (both thermoplastic and thermoset materials) and composites utilizing the same compliance mechanism as the porous polymer material.

The compliance indicator of FIGS. 3A-3B thus can be a dye encapsulated in a polymer which is released in the presence of oral fluids. The dye can be colorants that react with the oral fluids and that are released from the polymer. The polymer can be porous polymer such as monolithic porous polymer (currently used in chromatography), PVS, a high internal phase emulsion (HIPE polymer currently used in drug release), or any macroporous polymer. The dyed polymer will be constructed into a small button that can be bonded to the exterior of the aligner. The amount of dye loss will correspond with the amount of time the aligner was in use. The pore size of the polymer and the particle size of the dye will affect the rate of diffusion of dye from the button to the oral fluids environment and depending on compliance needs, these factors can be controlled.

Porous polymers are prepared by adding "porogens" during the polymerization process of resins. Porogens are soluble in the monomer but insoluble in formed polymers. As polymerization occurs, pores are formed in the spaces where porogens are found. The newest type of porous polymers is known as "high internal phase emulsions" ("HIPE"). HIPE structures have pore diameters much larger than previous porous materials which had only pore diameters in the angstroms.

Another porous polymer is the monolithic porous polymer currently being used in chromatography. The polymerization of this rigid macroporous polymer takes the shape of the mold, usually a column, into which the monomers and porogens are poured into. Generally, the pore volume is nearly equal to the amount of porogens added into the monoliths.

Figure 4A:
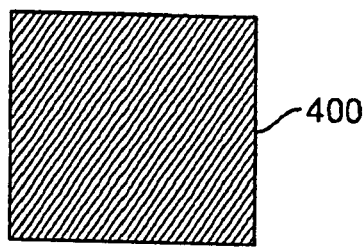
FIGS. 4A-4B show a third embodiment of the compliance indicator.
Figure 4B:

Referring now to FIGS. 4A and 4B, a button embodiment of an indication attachment device 400 is shown. In this embodiment, a biodegradable polymer material is attached to either a tooth or a dental appliance. After a certain period of use, the polymer material either changes shape or size or color, and as shown in FIG. 4B, the volume of the biodegradable polymer material is subsequently reduced. In some embodiments, the button is a biodegradable polymer button. The button can be molded from a biodegradable polymer and bonded to the exterior of the aligner. The button will have a predetermined degradation period such as a two week degradation period in the constant presence of oral fluids. Potentially the polymer can be colored for a more visible indication of the degradation of the button. The size and material will determine the degradation period of the button. However, other factors such as brushing of the aligner and rinsing will have to be taken into consideration when determining the optimal degradation time of the button.

The degradation products often define the biocompatibility of a polymer. Synthetic biodegradable polymers are favored over natural ones because of reliability of raw materials. The following is a list of common biodegradable polymers: polyglycolide (PGA), polylactide (PLA), l-lactide (LPLA), poly (dl-lactide) (DLPLA), poly(.epsilon.-caprolactone) (PCL), polydioxanone (PDO), poly(glycolide-co-trimethylene carbonate) (PGA-TMC), and polyorthoesters.

Figure 5:
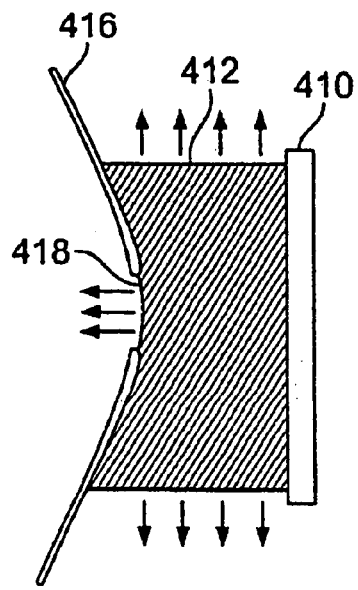
FIG. 5 shows a fourth embodiment of the compliance indicator.

FIG. 5 shows yet another embodiment of an indication attachment device. In this embodiment, an appliance 416 receives an adhesive dye matrix 412. The matrix 412 is sealed either at one end or both ends using a backing film 410. The material in the matrix 412 can be released on the sides between the appliance 416 and the film 410 or between the two backing films. An opening 418 may be provided in the appliance 416 and one side of the backing film to facilitate dye release. In one implementation, a transdermal patch may be applied in a manner similar to drug releasing transdermal patches. Instead of embedding and releasing drug in the adhesive matrix, a dye is released and the mechanism for dye loss is moisture (oral fluids). In one implementation, appliance wear compliance is indicated by the color of the adhesive layer: the more dye lost, the longer the wear time.

Figure 6:
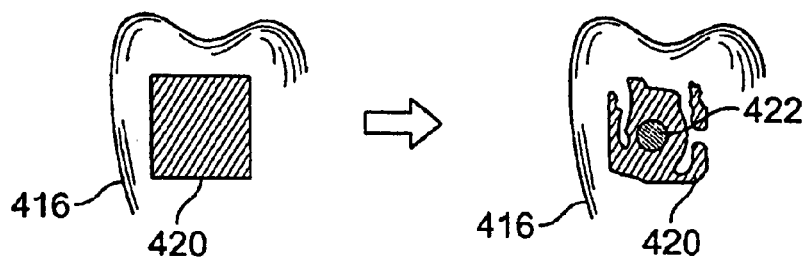
FIG. 6 shows a fifth embodiment of the compliance indicator.

FIG. 6 shows yet another embodiment where the wear indication is achieved through a water dissolvable film. In this embodiment, an opaque water soluble film 420 is positioned to cover one or more colored areas, regions, spots, or dots 422 on an appliance or on a tooth. The film can be a protective coating that can be used to protect the indicator (e.g., dot) from wear, such as from brushing teeth, etc. Since these appliances may be intended to be used for most of the day (e.g., 20+ hours), in many situations, protection of the indicator may be helpful in determining compliance.

In some embodiments, the protective coating can be removable and can be used to protect the indicators before and/or during application to an appliance or to one or more teeth. Such embodiments can also improve the accuracy of compliance analysis, in some instances.

In some embodiments, the dots 422 can be a series of colored dots with varying thicknesses of film 420 and each exposed color corresponds to a different amount of appliance wear time. In the embodiment where the dots 422 are imprinted on the appliance, the film 420 is layered onto the surface of the appliance. The mechanism of releasing dye is moisture (oral fluids).

Figure 7:
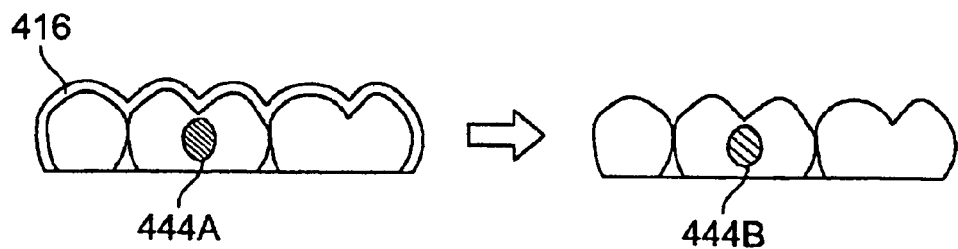
FIG. 7 shows a sixth embodiment of the compliance indicator.

FIG. 7 shows another embodiment where a tooth attachment 444A is made with a dye-releasing composite. The dye-releasing composite 444A bonded to a tooth will be covered by an appliance 416. Over time, the dye-releasing composite 444A has a reduced or no color loss compared to the loss for a dye on an uncovered tooth attachment 444B. The color of the attachment will correspond to the amount of aligner wear. The mechanism of dye releasing is moisture (oral fluids) in this embodiment.

In yet other implementations, a diagnostic indicator can be provided. The diagnostic indicator is similar in device construction to the compliance indicator, and utilizes the inwards diffusion strategy, where biochemical analytes from the external environment are allowed to diffuse through the membrane to react with the contents within the reservoir chamber. Thus, biomarkers from the external environment diffuse through the membrane, and react with reagents inside the content to directly or indirectly induce color change or chemical change that can be quantified through human eye or laboratory testing or computerized vision systems. As more biomarkers diffuse into the diagnostic indicator, the content color changes, for example increases in brightness and value. Possible biomarkers include enzymes, pH, glucose, salt, oral film, plaque, microorganisms that may exist in the oral cavity and amount of oral fluids.

Figure 8:
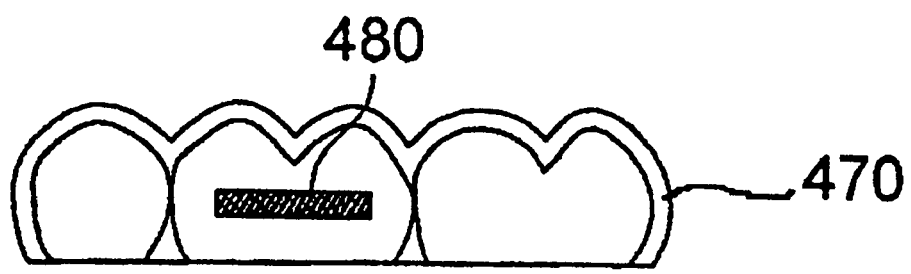
FIG. 8 shows a seventh embodiment of the compliance indicator.

In the embodiment shown in FIG. 8, the compliance indicator can be a time temperature indicator 480. The indicator 480 is intra-orally placed in the mouth (either directly on a tooth or on an appliance 470) and provides an indication of the time the indicator has been at a preselected intra-oral temperature environment.

Figure 9:
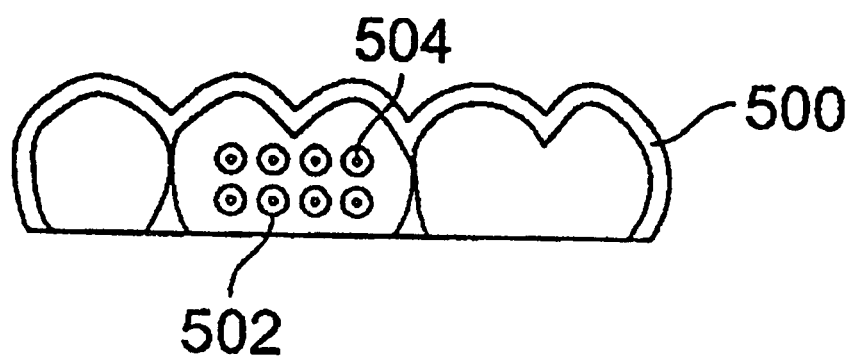
FIG. 9 shows an eighth embodiment of the compliance indicator.

In yet another embodiment shown in FIG. 9, a plurality of brushes 502 having a colored fiber 504 is positioned on the appliance 500. As the brush 502 is gradually eroded by wearing the appliance 500, a dye, or other suitable indicia of wear in the fiber 504 is exposed for visual detection by a human or by a machine. Alternatively, the brushes 502 can be placed on one or more teeth instead of on the appliance 500.

In yet another embodiment, the compliance indication is human readable by changing physical or mechanical or visual properties that are readily observable by a human. In other embodiment, the compliance indication is machine readable. For instance, in one embodiment that alters the electrical characteristics of an appliance during wearing of the appliance, an electrical measurement can be made by a computer for detecting compliance. In another embodiment that uses biomarkers, a computer with biomarker sensor can be used with suitable computer program to detect compliance. In yet another embodiment, a color change can be detected by a computer vision program to detect compliance.

Each computer program is tangibly stored in a machine-readable storage media or device (e.g., program memory or magnetic disk) readable by a general or special purpose programmable computer, for configuring and controlling operation of a computer when the storage media or device is read by the computer to perform the procedures described herein. The inventive system may also be considered to be embodied in a computer-readable storage medium, configured with a computer program, where the storage medium so configured causes a computer to operate in a specific and predefined manner to perform the functions described herein.

Portions of the system and corresponding detailed description are presented in terms of software, or algorithms and symbolic representations of operations on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" or "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission, or display devices.

FIG. 10 shows a number of appliances for use in various stages of a dental treatment process. FIG. 10 illustrates that a number of indicators can be placed on an appliance for use in a system. In the illustrated embodiment, three types of indicators 1090 (indicator type A), 1091 (indicator type B), and 1092 (indicator type C) are used in each stage 1015-1, 1015-2, and 1015-3. In some embodiments, more or less indicators can be used in each stage, the number of stages can be more or less, the number of indicators in each stage can be different, and/or the types of indicators can be different.

As discussed herein, a wear indicator can be a small layered disc which can be composed of a number of layers, in various embodiments, among other shapes and forms. For example, in some embodiments, the wear indicator can include three layers, such as a bonding layer, an active indicator layer, and a protective layer. In such embodiments, the bonding layer can, for example, be on the inner surface, the active indicator layer (e.g., wear layer) in the middle, and the protective layer on the outer surface, among other constructions.

The bonding layer can, for example, be composed of a biocompatible pressure-sensitive adhesive (e.g., acrylic, silicone, and/or polyisobutene) which can allow for adhesion of the indicator to the aligner surface, or other suitable surfaces. The wear layer can, for example, be composed of a water-soluble polymer (e.g., high molecular weight polyvinyl alcohol) mixed with a FD&C (FDA certified) "aluminum lakes" dye which allows for leaching of the color over a period of time, among other materials.

The concentrations of these materials and/or use of other materials can be utilized to provide a number of different wear rates. Although the wear rates of these indicators may not be standardized from one patient to another, the wear rates of these indicators can be predetermined with respect to each other. In such embodiments, indicators of various wear rates with respect to each other can be utilized. Such wear indicators can be used as compliance indicators or as treatment disbursement apparatuses (e.g., for the disbursement of agents as described herein) as the wearable material wears during use of the appliance to which it is associated.

These wear rates can be established, for example, by exposing the wear indicator to a uniform reactant (e.g., a material that causes the indicator to change). The periods of change to the indicators can be measured and can, therefore, be used to set the amount of expected change with respect to the other indicators similarly tested.

The protective layer can, for example, be a film (e.g., transparent) that protects the active indicator layer from tooth brushing, buccal and/or lingual contact, and/or other external forces. In some embodiments, the protective layer can be used to protect the indicator during shipment or application and can, in some embodiments, be removable during wear and/or before or during application.

In the embodiment illustrated in FIG. 10, the patient can be given the appliances for stages 1, 2, and 3, for use as directed by the treatment professional. After a period, the patient will return the appliances for inspection. Once inspected, the treatment professional can select the appropriate indicator for subsequent stages for that patient's treatment based upon the amount of wear indicated by the one or more indicators on one or more of the appliances.

In the embodiment of FIG. 10, three wear indicators were used to adjust the compliance indicator or treatment disbursement wear rate. When different types of wear indicators are used, it can be beneficial, for example, in order to include a range of wear rates that may include a large portion of the patient population, which may have very large variations in wear rate from one patient to the next.

For example, initial testing identified that there may be many variables and differences in each patient's oral environment and, therefore, one type of wear indicator may not likely be enough to last for a desired period of wear in every person. Some examples of the type of wear that determines the wear rate of the wear layer can determined based upon one of the factors selected from the group including amount of saliva produced, one or more tooth anatomies or locations, a composition of saliva, an analysis of sleep habits of a patient, an amount of liquid consumption, and one or more types of liquid consumed, among other criteria.

In some embodiments, patients can utilize a wide range of types of wear indicators initially to determine which one best indicates their compliance and physiological profile. Patients can then continue using one or more types of indicators and their compliance can be evaluated based on each individual patient's predetermined baseline rate determined based upon the wear of the initial indicators. In this way, one or more wear indicators can be used as an indicator of a patient's compliance to the orthodontic program if the wear rate with respect to that patient is understood.

In some embodiments, multiple wear indicators of the same type can be utilized in various positions on the appliance. Such arrangements can be used to further precision the placement if the wear indicators used for compliance and/or for treatment disbursement, as discussed further below. Examples of different placement positions can, for example, include positions that compare buccal and lingual positions, molar and anterior positions, gingival and occlusal positions, and/or other comparisons of such positions, or other suitable positions in addition to or in substitution for those described above.

For instance, in some embodiments, a system for monitoring orthodontic treatment can include a first appliance for placement over one or more teeth The appliance can include multiple wear indicators including at least a first positional indicator (i.e., a wear indicator that is used to analyze the suitability of a position within the mouth) having a wear rate and a second positional indicator that having a wear rate, where the wear rates of the first and second positional indicators are the same and where the first positional indicator is placed in a position on the first appliance that is different from the second positional indicator. In some embodiments, the position of a third wear indicator on a second appliance can be determined based upon analysis of the first and second indicators positioned on the first appliance in positions selected from buccal, lingual, molar, anterior, gingival, and/or occlusal positions, among others.

In treatment disbursement apparatus embodiments, the wear indicators can be used to determine the wear rate for proper treatment disbursement to a particular patient. This allows dosages to be more effectively tailored to particular patient needs, in some instances. This can, for example, be accomplished by review of the wear indicators after a period of time and evaluation of which indicator has worn most effectively (e.g., longest wear, most uniform wear, etc.) over the period.

The positions of the different indicators can also be used, in some embodiments, to determine where a suitable location may be for proper disbursement of a treatment by examination of the wear indicators after a period of time and determination, based upon the observed wear, what one or more locations would be suitable. In some instances, the wear indicators may have the same wear rate for such determinations.

The analysis of compliance can be accomplished in any suitable manner based upon the information provided by the initial indicators. For example, in some embodiments, determining a type of compliance indicator to be placed on a subsequent dental appliance can be based upon a comparison of two or more compliance indicators after the appliance has been used by a patient for a set period of time. In such embodiments, an initial indicator can be compared with an indicator that is used in a subsequent stage, for example.

In some embodiments, determining a type of compliance indicator to be placed on a subsequent dental appliance can be based upon a comparison of one or more compliance indicators with a baseline wear rate after the appliance has been used by a patient. In such embodiments, the baseline can be determined based upon the information provided by the initial indicators.

FIG. 11 shows a table indicating the meaning of various combinations of wear on appliance indicators. In FIG. 11, the table includes a column 1193 that provides the wear of each of the indicators on the appliance (e.g., indicators 1090 (indicator type A), 1091 (indicator type B), and 1092 (indicator type C) of FIG. 10). In the example of FIG. 11, indicator C is designed to wear the fastest, indicator B is designed to wear slower that indicator C, but faster that indicator A, and indicator A is designed to wear the slowest.

In some embodiments, the positions of the indicators may not be not utilized. However, in some embodiments, this information may be utilized for various purposes, such as the position for greatest/least amount of wear can be measured or what type of indicator may work best to determine compliance for a particular patient and/or for treatment disbursement. For example, in the embodiment of FIG. 11, the bottom right indicator represents indicator type A 1090, the bottom left indicator represents indicator type B 1091, and the top indicator represents indicator type C 1092 of FIG. 10.

For example, in the top row of the table, the top indicator is dark blue, the left is dark blue, and the right is light blue. Accordingly, since the top and left indicators have not changed and the right indicator has changed, the right indicator would be a good choice for monitoring this particular patient and/or for treatment disbursement. The right indicator corresponds to indicator type A 1090 in FIG. 10 and, accordingly, the instructions in row one of column 1194 indicate that an A indicator is to be used, with a baseline being faded (e.g., light blue).

The set of indicator results of the top row of the table indicates that the wear experienced with this patient is light. As discussed above, this can be attributable to various issues. However, if this row is selected, the table can be used to provide direction with respect to which type of indicator to provide for additional stages and/or what type of baseline should be used with this patient.

In the second row of the table of FIG. 1, the top indicator is dark blue, the left is dark blue, and the right is white. Accordingly, as with the above example, since the top and left indicators have not changed and the right indicator has changed, the right indicator would be a good choice for monitoring this particular patient and/or for treatment disbursement. Again, in the embodiment of FIG. 11, the right indicator corresponds to indicator type A 1090 in FIG. 10 and, accordingly, the instructions in row two of column 1194 indicate that an A indicator is to be used, with a baseline being faded (e.g., light blue).

In the third row of the table of FIG. 11, the top indicator is dark blue, the left is light blue, and the right is white. With this type of indicator arrangement, since the top is still dark and the right is white (e.g., indicating that the indicator has been excessively worn), the right indicator would be a good choice for monitoring this particular patient and/or for treatment disbursement, because it still has some wear remaining. In the embodiment of FIG. 11, the right indicator corresponds to indicator type B 1091 in FIG. 10 and, accordingly, the instructions in row three of column 1194 indicate that a B indicator is to be used, with a baseline being faded (e.g., light blue).

Although the table in FIG. 11 provides some recommendations on the selection of an indicator based upon the results of the initial indicator usage, the treatment professional may use their judgment in selecting a particular indicator type. In some such embodiments, indicator A may be designated for use in subsequent appliances. However, in some instances, the indicator may wear out much sooner than the period between check by a treatment professional and, therefore, the timeframe of compliance and/or for treatment disbursement may likely have to be estimated.

The treatment professional could also chose to use indicator C in some instances. However, the indicator may not indicate any change during the period between checks and, therefore, compliance may not be able to be ascertained.

In the fourth row of the table of FIG. 1, the top indicator is dark blue, the left is white, and the right is white. With this type of indicator arrangement, since the top is still dark and the left and right are white (e.g., indicating that the indicator has been excessively worn), the left indicator would be a good choice for monitoring this particular patient and/or for treatment disbursement. This is because in the embodiment represented by the table of FIG. 11, indicator type B 1091 has a slower wear rate than indicator type A 1090 and, therefore, will wear longer than indicator type A 1090. Accordingly, the instructions in row four of column 1194 indicate that a B indicator is to be used, with a baseline being clear (e.g., white).

In the fifth row of the table of FIG. 1, the top indicator is light blue, the left is white, and the right is white. With this type of indicator arrangement, since the top is the only indicator showing some wear is left and, therefore, the top indicator would be a good choice for monitoring this particular patient and/or for treatment disbursement, because it still has some wear remaining. In the embodiment of FIG. 11, the top indicator corresponds to indicator type C 1092 in FIG. 10 and, accordingly, the instructions in row five of column 1194 indicate that a C indicator is to be used, with a baseline being faded (e.g., light blue).

In the last row of the table of FIG. 11, all the indicators are white. With this type of indicator arrangement, since the all indicators are white (e.g., indicating that the indicator has been excessively worn), the top indicator would be a good choice for monitoring this particular patient and/or for treatment disbursement, since it wears the slowest. This is because in the embodiment represented by the table of FIG. 11, indicator type C 1092 has the slowest wear rate than either of the indicators 1090 and 1091 (indicator types A and B) and, therefore, will wear longer than indicators 1090 and 1091 (indicator types A and B).

Accordingly, the instructions in row six of column 1194 indicate that a C indicator is to be used, with a baseline being clear (e.g., white). This last set of results may also indicate that one or more even slower wearing indicators should be used to identify if those indicators would have some wear remaining. Such slower wearing indicators could be provided in one or more subsequent stages, for example.

As discussed above, in the embodiment illustrated in FIG. 11, the embodiment includes multiple indicators (e.g., three in FIG. 11). Although illustrated in a particular order, the indicators can be positioned in any suitable order or position.

In some such embodiments, for example, an appliance for placement over one or more teeth can be provided and multiple wear indicators can be utilized therewith (e.g., including at least a first wear indicator having a first wear rate and a second wear indicator that has a second wear rate that is different from the first). For example, an indicator can be sprayed, formed, adhered, or otherwise affixed to the appliance or provided with the appliance.

In some embodiments, using three or more indicators can provide greater versatility in the time period of compliance by the patient and/or for treatment disbursement. For example, multiple indicators each having different wear rates can allow a treating professional to more accurately pinpoint the amount of usage of the device.

For instance, one indicator can become fully worn in five days, a second can be fully worn in ten days, and a third can be fully worn in fifteen days. In such embodiments, the treating professional may be able to more accurately tell how much usage has been done by the patient because of the discrete nature of each of the indicator's wear patterns.

In some such embodiments, the system can include one or more of the multiple wear indicators mounted on the appliance to indicate compliance and/or the amount of treatment disbursement that has been done by demonstrating a change in at least one characteristic of the indicator. The changed characteristic can, for example, be a color, shape, and/or size, among others. In some embodiments, compliance and/or disbursement can be indicated by an absence of a change.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the use of the terms "a", "an", "one or more", "a number of", or "at least one" are all to be interpreted as meaning one or more of an item is present. Additionally, it is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in a single embodiment for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow. For example, although films or appliances have been disclosed as mechanisms for compliance measurement, droplets can be used to deliver the compliance indicating substances to the patient as well. Other embodiments for compliance indication can be used as well. Whereas particular embodiments of the present invention have been described herein for purposes of illustration, it will be evident to those skilled in the art that numerous variations of the details may be made without departing from the invention as defined in the appended claims.

We claim:

1. A system for monitoring orthodontic treatment comprising:
   a first appliance for placement over one or more teeth; and
   multiple wear indicators including at least a first wear indicator having a first wear rate and a second wear indicator that has a second wear rate that is different from the first wear rate;
   wherein the multiple wear indicators each include:
      a bonding layer on an inner surface of the wear indicator that is adhesively coupled to the first appliance and comprised of a material different than a material comprising the first appliance; and
      an active indicator layer on an outer surface of the bonding layer including a water-soluble polymer.

2. The system of claim 1, where at least one of the multiple wear indicators is mounted on the first appliance to indicate compliance by demonstrating a change in at least one characteristic of the indicator, wherein the changed characteristic comprises at least one of color, shape, and size.

3. The system of claim 2, where the change is affected by at least one of moisture, temperature, one or more chemicals and one or more biological substances.

4. The system of claim 1, where at least one of the multiple wear indicators is mounted on the first appliance to indicate treatment distribution by demonstrating a change in at least one characteristic of the indicator, wherein the changed characteristic comprises at least one of color, shape, and size.

5. The system of claim 1, where the system includes:
a second appliance for placement over one or more teeth; and
at least one compliance indicator having a wear rate based upon an analysis of the first and second wear rates associated with the first appliance.

6. The system of claim 1, where the system includes:
a second appliance for placement over one or more teeth; and at least one treatment distribution apparatus having a wear rate based upon an analysis of the first and second wear rates associated with the first appliance.

7. The system of claim 1, where the compliance is indicated by a release of a colorant within the appliance.

8. The system of claim 1, where the change is affected by a degradation of a biodegradable or a dissolvable polymer.

9. The system of claim 1, where the compliance is indicated by a loss in size of the indicator.

10. The system of claim 1, including a number of second wear indicators positioned on a second appliance, where the number of second wear indicators includes at least a first positional indicator having a wear rate and a second positional indicator having a wear rate, where the wear rates of the first and second positional indicators are the same and where the first positional indicator is placed in a position on the second appliance that is different from the second positional indicator.

11. An apparatus for monitoring orthodontic treatment, comprising:
an appliance for placement over one or more teeth; and
multiple wear indicators including at least a first wear indicator having a first wear rate and a second wear indicator that has a second wear rate that is different from the first, where at least one of the multiple wear indicators is mounted on the appliance to indicate wear by demonstrating a change in at least one characteristic of the indicator;
wherein the multiple wear indicators each include:
a bonding layer on an inner surface of the wear indicator that is adhesively coupled to the first appliance and comprised of a material different than a material comprising the first appliance; and
an active indicator layer on an outer surface of the bonding layer including a water-soluble polymer.

12. The apparatus of claim 11, where at least one of the multiple wear indicators is mounted on the appliance to indicate compliance by demonstrating a change in at least one characteristic of the indicator;
where the active indicator layer of the at least one of the multiple wear indicators includes a colored material mixed with the water-soluble polymer; and
where the active indicator layer of the at least one of the multiple wear indicators is configured to indicate compliance by leaching the colored material.

13. The apparatus of claim 12, where the multiple wear indicators are three or more indicators attached to the appliance.

14. The apparatus of claim 11, where at least one of the multiple wear indicators is mounted on the appliance to indicate compliance by demonstrating a change in at least one characteristic of the indicator and where compliance is indicated by an absence of a change while the appliance is worn.

15. The apparatus of claim 11, where at least one of the multiple wear indicators is mounted on the appliance to indicate compliance by demonstrating a change in at least one characteristic of the indicator and where the compliance is indicated by a color change.

16. The apparatus of claim 15, where the color change occurs due to a reaction between one or more materials in the indicator and one or more oral fluids.

17. The apparatus of claim 11, where at least one of the multiple wear indicators is mounted on the appliance to indicate compliance by demonstrating a change in at least one characteristic of the indicator and where the compliance is indicated by a mechanical deformation during orthodontic movement.

18. A method for monitoring orthodontic treatment, comprising:
affixing a first wear indicator having a first predetermined wear rate relative to a second, different, predetermined wear rate of a second wear indicator onto a first dental appliance to be worn by a patient during a first period of time;
affixing the second wear indicator onto the first dental appliance;
determining a particular wear rate relative to the first and the second predetermined wear rates sufficient to indicate compliance over a second period of time subsequent to the first period of time during which the patient will wear a second dental appliance based on a comparison of wear of the first and the second wear indicators after use by the patient during the first period of time; and
affixing a particular wear indicator having the particular wear rate onto the second dental appliance.

19. The method of claim 18, where the particular wear rate is equal to one of the first wear rate or the second wear rate.

20. The method of claim 18, where the particular wear rate is different than the first and the second wear rates.

21. The method of claim 18, where the method includes determining a baseline wear rate specific to the patient based upon a comparison of wear of the first and the second wear indicators after use by the patient during the first period of time.

22. The method of claim 18, where the method includes:
affixing a third wear indicator having a third predetermined wear rate different than and relative to the first and the second predetermined wear rates onto the first dental appliance to be worn by a patient during the first period of time; and
determining a particular wear rate relative to the first, the second, and the third predetermined wear rates sufficient to indicate compliance over the second period of time subsequent to the first period of time during which the patient will wear the second dental appliance based on a comparison of wear of the first, the second, and the third wear indicators after use by the patient during the first period of time.

23. A dental appliance, comprising:
an appliance for placement over one or more teeth; and
a dental appliance indicator coupled to the appliance, including:

an adhesive layer on an inner surface of the dental wear indicator configured to be adhesively coupled to the appliance;

a wear indicator layer including a water-soluble polymer on an outer surface of the adhesive layer having a predetermined wear rate; and a protective layer on the wear indicator layer.

24. The dental appliance of claim 23, where the protective layer is a transparent film configured to protect the wear indicator layer from external forces.

25. The dental appliance of claim 23, where a type of wear that determines the wear rate of the wear indicator layer is determined based upon one of the factors selected from the group including:
- amount of saliva produced;
- one or more tooth anatomies or locations;
- a composition of saliva;
- an analysis of sleep habits of a patient;
- a amount of liquid consumption; and
- one or more types of liquid consumed.

26. A system for monitoring orthodontic treatment comprising:

a first appliance for placement over one or more teeth; and multiple wear indicators including at least a first positional indicator having a wear rate and a second positional indicator having a wear rate, where the wear rates of the first and second positional indicators are the same and where the first positional indicator is placed in a position on the first appliance that is different from the second positional indicator;

wherein the multiple wear indicators each include:
- a bonding layer on an inner surface of the wear indicator that is adhesively coupled to the first appliance and comprised of a material different than a material comprising the first appliance; and
- an active indicator layer on an outer surface of the bonding layer including a water-soluble polymer.

27. The system of claim 26, where a position of a third wear indicator on a second appliance is determined based upon analysis of the first and second indicators positioned on the first appliance in positions selected from the group including: buccal, lingual, molar, anterior, gingival, and occlusal positions.

* * * * *